United States Patent [19]

Fjellestad-Paulsen

[11] Patent Number: 5,780,434
[45] Date of Patent: Jul. 14, 1998

[54] COMPOSITION FOR ORAL ADMINISTRATION OF PEPTIDES

[75] Inventor: Anne Fjellestad-Paulsen, Paris, France

[73] Assignee: Ferring B.V., Netherlands

[21] Appl. No.: 525,584

[22] PCT Filed: Mar. 18, 1994

[86] PCT No.: PCT/SE94/00244
§ 371 Date: Sep. 19, 1995
§ 102(e) Date: Sep. 19, 1995

[87] PCT Pub. No.: WO94/21286
PCT Pub. Date: Sep. 29, 1994

[30] Foreign Application Priority Data

Mar. 19, 1993 [SE] Sweden .................. 9300937

[51] Int. Cl.$^6$ .............. A61K 9/20; A61K 9/48; A61K 38/11; A61K 47/42

[52] U.S. Cl. .................. 514/15; 424/452; 424/465; 514/807

[58] Field of Search .................. 530/315, 313; 514/15, 807, 970, 973; 424/452, 463, 465, 480, 482, 494, 495, 497

[56] References Cited

U.S. PATENT DOCUMENTS

| 4,139,504 | 2/1979 | Coy et al. | 514/15 |
| 4,849,227 | 7/1989 | Cho | 424/498 |
| 5,047,398 | 9/1991 | Hagstam et al. | 514/15 |
| 5,120,710 | 6/1992 | Liedtke | 514/3 |
| 5,206,219 | 4/1993 | Desai | 514/3 |
| 5,534,494 | 7/1996 | Bowers et al. | 514/15 |

FOREIGN PATENT DOCUMENTS

| 127535 | 12/1984 | European Pat. Off. |
| 130779 | 1/1985 | European Pat. Off. |
| 507573 | 10/1992 | European Pat. Off. |
| 3-86834 | 4/1991 | Japan |

OTHER PUBLICATIONS

M.E.K. Kraeling et al., "Development of A Colonic Release Capsule Dosage Form and the Absorption of Insulin", Meth Find Exp Clin Pharmacol, vol. 14, No. 3, 1992, pp. 199–209.

M. Saffran et al., "A Model for the Study of the Oral Administration of Peptide Hormones", Canadian Journal of Biochemistry, vol. 57, 1979, pp. 548–553.

R.S. Geary et al., "Vancomycin and Insulin Used as Models for Oral Delivery of Peptides", Journal of Controlled Release, vol. 23, 1993, pp. 65–74.

A.N. Elias et al., "Effective Portal Insulin Delivery With Enzyme-Protected Capsules in Pancreatectomized Pigs", Gen. Pharmac., vol. 23, No. 1, 1992, pp. 55–59.

Primary Examiner—Jeffrey E. Russel
Attorney, Agent, or Firm—Ostrolenk, Faber, Gerb & Soffen, LLP

[57] ABSTRACT

A solid pharmaceutical composition for oral administration of small and medium size peptides, particularly vasopressin, oxytocin, and their analogues, comprises the peptide, a protease inhibitor, an enteric coat and a pharmaceutically acceptable carrier containing a buffering agent buffering at a pH of from 3 to 6, preferably about pH 5. A method of manufacture of single doses of the peptide comprises mixing of the ingredients, forming the resulting mixture into spheres smaller than 2 mm, coating the spheres with an enteric coat which is readily soluble in gastric juice of pH 5.0 or higher but not at substantially lower pH, and filling the coated spheres in capsules or incorporating them into tablets, degradable in the stomach. Also disclosed is a method for oral administration to a patient of the single dose.

10 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /product="OTHER"
          / note= "D-ethyl-tyrosine"

( i x ) FEATURE:
        ( A ) NAME/KEY: Modified-site
        ( B ) LOCATION: 8
        ( D ) OTHER INFORMATION: /product="Orn"

( i x ) FEATURE:
        ( A ) NAME/KEY: Modified-site
        ( B ) LOCATION: 1
        ( D ) OTHER INFORMATION: /product="OTHER"
          / note= "mercaptopropionic acid"

( x i ) SEQUENCE DESCRIPTION: SEQ ID NO:1:

Xaa Tyr Ile Thr Asn Cys Pro Xaa Gly
        1                 5

( 2 ) INFORMATION FOR SEQ ID NO:2:

```
( i ) SEQUENCE CHARACTERISTICS:
    ( A ) LENGTH: 9 amino acids
    ( B ) TYPE: amino acid
    ( C ) STRANDEDNESS: Not Relevant
    ( D ) TOPOLOGY: Not Relevant ( i i ) MOLECULE TYPE: peptide ( i x ) FEATURE:
    ( A ) NAME/KEY: Modified-site
    ( B ) LOCATION: 2
    ( D ) OTHER INFORMATION: /product="OTHER"
          / note= "N-methyl-tyrosine"

( i x ) FEATURE:
    ( A ) NAME/KEY: Modified-site
    ( B ) LOCATION: 1
    ( D ) OTHER INFORMATION: /product="OTHER"
          / note= "butyric acid"

( x i ) SEQUENCE DESCRIPTION: SEQ ID NO:2:

Xaa  Tyr  Ile  Gln  Asn  Cys  Pro  Leu  Gly
    1                  5

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Modified-site
        ( B ) LOCATION: 8
        ( D ) OTHER INFORMATION: /product="OTHER"
              / note= "D-arginine"

( i x ) FEATURE:
        ( A ) NAME/KEY: Modified-site
        ( B ) LOCATION: 1
        ( D ) OTHER INFORMATION: /product="OTHER"
              / note= "mercaptopropionic acid"

( x i ) SEQUENCE DESCRIPTION: SEQ ID NO:3:

Xaa  Tyr  Phe  Gln  Asn  Cys  Pro  Arg  Gly  Gly
    1                  5                        10

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

Cys  Tyr  Ile  Asn  Cys  Pro  Leu  Gly
    1                  5
```

COMPOSITION FOR ORAL ADMINISTRATION OF PEPTIDES

FIELD OF THE INVENTION

The present invention relates to pharmaceutical compositions in solid form for oral administration of small and medium size peptides, particularly vasopressin, oxytocin, and their analogues. The present invention also relates to a method of manufacturing a single dose of said composition for oral administration of small and medium-size peptides, particularly vasopressin, oxytocin, and their analogues.

The invention further relates to a method of administering said composition to a patient.

BACKGROUND

A number of medicines for treatment of a variety of diseases contain, as the active ingredient, naturally occurring peptides or their synthetic analogues.

Saffran et al. (can. J. Biochem. 57 (1979) 548–522) described a Sprague Dawley rat model for the study of the oral administration of peptide hormones. Urine retention after gastric administration of an aqueous solution of the vasopressin analog (1-deamino-4-valine)-8-D-arginine-vasopressin was found to be moderately enhanced in the presence of aprotinin.

Similarly, EP-A2 127 535, EP-A2 130 779, EP-A2 507 573, and J. Controlled Release 23 (1993) 56–74 (R. S. Geary and H. W. Schlameus), disclose the use of peptidase inhibitors as ingredients in solid pharmaceutical compositions containing biologically active peptides and their analogues. The aforementioned compositions, EP-A2 127 535, EP-A2 130 779, EP-A2 507 573, J. Controlled Release 23 (1993) 65–74 (R. S. Geary and H. W. Schlameus) have been designed, by providing them with an appropriate enteric coat, for release of their active ingredients in the small intestine, where some peptides, particularly insulin, are known to be better absorbed.

Because of the instability of small and medium size peptides, particularly vasopressin, oxytocin, and their analogues, in the environment of the gastrointestinal tract their uptake, when given as a medicine or for similar reasons, is still very unsatisfactory. Thus, better delivery systems for non-parenteral, particularly oral, administration of peptides and their analogues are desirable, cf. Davies, S.: "Developing delivery systems for peptides and proteins", Scrip Magazine 1992, 34–38.

OBJECTS OF THE INVENTION

It is an object of the present invention to provide a pharmaceutical composition which provides for better absorption of said small or medium-size peptides, particularly vasopressin, oxytocin, and their analogues.

It is another object of the present invention to provide a method of manufacture of a single dose of said pharmaceutical composition for oral administration of small and medium-size peptides, particularly vasopressin, oxytocin, and their analogues.

It is a further object of the invention to provide a method of administration of said composition to a patient.

Additional objects of the present invention will become evident by study of the detailed description of preferred embodiments of the invention.

SUMMARY OF THE INVENTION

The above and other objects of the invention are provided by a pharmaceutical composition of the kind described above, said composition comprising small and/or medium size peptides, particularly vasopressin, oxytocin, or an analog of vasopressin or oxytocin; a protease inhibitor; an enteric coat; and a pharmaceutically acceptable carrier containing a buffering agent buffering at a pH of from 3 to 6, preferably at about pH 5.

It is preferred for the protease inhibitor to be natural or structurally modified aprotinin. Other specific and unspecific protease inhibitors may be used; it is also possible to use mixtures of protease inhibitors. The expert will select the protease inhibitor(s), particularly serine protease inhibitors, suitable for protecting the respective peptide in the particular gastrointestinal environment. Besides native aprotinin isolated from natural sources, such as, for instance, native bovine aprotinin isolated from bovine lungs or pancreas, useful serine proteinase inhibitors comprise aprotinin and aprotinin analogues encoded by synthetic genes expressed in, e.g., yeast (Norris, K. et al., Biol. Chem. Hoppe-Seyler 371 (1990) 37–42) and E. coli (Brinkmann, T. and Tschesche, H. ibid. 43–52), and chymostatin.

It is preferred for the peptide to be chosen from DDAVP (desmopressin), oxytocin, atosiban, and carbetocin. Particularly preferred is DDAVP. For full sequences of these peptides, see Table 1 at the end of the DETAILED DESCPRIPTION section. Another group of peptides preferred for oral administration by incorporation into the composition according to the invention comprises GnRH-analogues (gonadotropin-releasing hormone analogues) such as gonadorelin and triptorelin.

It is preferred for the pharmaceutically acceptable carrier to further comprise one or several agents selected from the group consisting of carbohydrates and modified carbohydrates and derivatives thereof, polyethylene and/or polypropylene glycol and derivatives thereof, inorganic fillers or lubricating agents, fatty acids and their esters and salts, preservatives and coating agents. Suitable pharmaceutically acceptable carriers comprise a wide variety of carriers for production of pharmaceutical formulations in tablet or capsule form, e.g. the carrier of the antidiuretic composition containing DDAVP disclosed in the European patent no. 163 723. Especially preferred are multiparticle systems, such as systems for administration in soft and hard gelatin capsules; preferred particle sizes for spheres containing peptide and/or protease inhibitor are below about 2 mm.

According to a preferred aspect of the invention, the enteric coat is designed for release of its contents in the small intestine. It is particularly preferred for the particles contained in the tablets or capsules to be coated with an enteric coating for delayed release of their contents in the upper part of the small intestine. Especially preferred is delayed release of the peptide and the protease inhibitor in the duodenum and the jejunum, particularly in the duodenum and the upper jejunum. The enteric-coated spheres may also be contained in a tablet that readily disintegrates in the stomach or may be administered in suspended form in media that will not readily dissolve the enteric coating. It is also possible for the peptide and the protease inhibitor to be contained in separate spheres having the same type of enteric coating.

It is preferred for the enteric coat to be soluble in gastric juice at a pH of about 5.0 or higher; particularly preferred is a pH of about 5.5 or higher. Enteric coatings that are not readily dissolvable in such fluids at a pH of about 6.5, however, will not permit substantial release of the ingredients of the composition, according to the invention, in the upper small intestine and, therefore, are not preferred; on the other hand, coatings that dissolve in gastric fluids at a pH substantially lower than 5.0 are less preferred since they will release the ingredients in the stomach. Useful enteric coatings according to the invention comprise polymers having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers, as well as polyvinylacetate phthalates and similar partial esters of dibasic or tribasic carboxylic acids with polyvinylacetate and similar polymers carrying alcohol hydroxyl groups. The enteric coating may also advantageously be prepared from mixtures of such polymers.

The peptide and/or the protease inhibitor is preferably admixed with a carrier comprising a buffering agent and one or several agents selected from the group consisting of carbohydrates and modified carbohydrates and derivatives thereof, polyethylene and/or polypropylene glycol and derivatives thereof, organic and inorganic core, filler or lubricating materials, fatty acids, their esters and salts, preservatives, antioxidants, and coating agents. The buffering agent should be able to buffer at a pH from about 3 to about 6, preferably at about pH 5.5, i.e. to exert substantial buffer capacity within this range and preferably at about pH 5.5. Since the composition according to the invention is intended for preferred release in the upper part of the small intestine where, during their passage, the acidic contents of the stomach are neutralized by influx of $Na^+$, buffering inhibits or delays an increase of pH exceeding the preferred range or, in other words, in the direction of the upper limit of the preferred range and exceeding its upper limit. Preferred buffering agents are hydrogen and dihydrogen phosphates, such as sodium dihydrogen phosphate and mixtures of sodium dihydrogen phosphate with disodium hydrogen phosphate, calcium tetrahydrogen phosphate, citric acid and mixtures of citric acid and its monosodium salt, fumaric acid and its monosodium salt, adipic acid and its monosodium salt, tartaric acid and its sodium salt, ascorbic acid and its monosodium salt, glutamic acid, aspartic acid, betaine hydrochloride, hydrochlorides of amino acids, such as arginine monohydrochloride and glutamic acid hydrochloride, and saccharic acid. It is preferred for the buffering agent to comprise at least 10% by weight, more preferred at least 25% by weight, most preferred at least 40% by weight of the composition according to the invention. A mixture of two or more buffering constituents can be used.

According to the invention there is also provided a method of manufacture of single doses of the composition according to the invention, said method comprising the following steps:

mixing the peptide, the proteinase inhibitor and a suitable carrier including a buffering agent, buffering in the range from pH 3 to pH 6, preferably at about pH 5, spheronizing the mixture for formation of spheres with a diameter smaller than about 2 mm, coating the spheres with an enteric coat which is readily soluble in gastric juice of pH 5.0 or higher but not readily soluble at substantially lower pH, filling the coated spheres in capsules or incorporating them into tablets, said capsules or tablets being readily disintegrable in the stomach.

The invention further relates to a method for administration of a single dose of a small and medium-size peptide, particularly vasopressin, oxytocin, and their analogues, to a patient, comprising administering orally to the patient, a tablet or capsule containing a pharmacologically effective amount of said small and medium-size peptide in form of the composition according to the invention, said tablet or capsule being disintegrable in the stomach.

DETAILED DESCRIPTION

The invention will now be described in greater detail by reference to degradation of DDAVP in gastric juice.

EXAMPLE 1

Human gastro-intestinal juice was obtained from healthy male volunteers who had been fasting for 8 h. A tube was introduced intranasally after local anaesthesia with xylocaine, and gastric juice was collected. Thereafter one standardized meal was given 1 h before sampling of duodenal and distal jejunum juice and another the next morning before the collection of distal ileal juice. After centrifugation the gastric and intestinal juices were frozen in aliquots of 1 ml and stored at −20° C.

Degradation method. The peptide or peptide analog (10 μl of 10 mM peptide in 0.9% aqueous NaCl) was added to 190 μl of undiluted juice at 37° C. Aliquots of 25 μl were withdrawn at intervals and mixed with 100 μl acetone to stop the reaction. After centrifugation for 10 min at 10,000 g, 10 μl of the supernatant was analyzed by reversed phase HPLC. The effects of increasing amounts of aprotinin were examined under the above conditions in intestinal juice from the ileum.

Determination of peptide degradation. Analysis was carried out in a Varian 5000 HPLC analyzer equipped with a UV-detector (220 nm). Column Bondapak TM C18 (3.9× 300 mm), eluant MeOH/0.025M $NH_4Ac$ (isocratic conditions), flow rate 1 ml/min.

Protein and pH determination. Protein: Bio-Rad protein assay. pH: Orion model SA720; pH-paper Merck (Darmstadt), range 4.0–7.0.

Results. DDAVP was found to be degraded (to about 50% after 35 min) by both gastric and intestinal juices at pH 6.5. When the pH was adjusted to 4.0 DDAVP appeared to be essentially stable. A concentration-dependent inhibition was observed in the presence of aprotinin at pH 6.5. Absent pH-adjustment, DDAVP proteolysis was found to be slower in jejunal or duodenal juice than in ileal juice. The surprisingly pronounced in-vitro activity of aprotinin translates into more active peptide being available for uptake by the intestinal wall.

EXAMPLE 2

Experiments with healthy volunteers. After having fasted for 8 hours six healthy male volunteers were intubated (cf. example 1) with quadruple lumen flexible PVC tubes. The open end of the tube was positioned in the duodenum close to the pylorus; correct positioning was verified fluoroscopically. DDAVP acetate (0.4 mg in 2 ml 0.9% aqueous sodium chloride) was applied at the start and the tube was rinsed with 2 ml 0.9% aqueous sodium chloride. Perfusion with aprotinin (ANTAGOSAN™, Hoechst, Germany; aqueous solution, 10,000 kallikrein inactivator units/ml) started immediately after application of DDAVP and continued for 4 h at a rate of 5 ml/min. A standard breakfast was given 5–10 min after application of DDAVP, and a standardized meal 4 h later. From 2 h after start onwards the volunteers were given 100 ml/h water orally. Each volunteer participated in three sessions.

Blood samples were drawn into EDTA K VACUTAINER™ tubes, cooled immediately and centrifuged at 40° C. for determination of the plasma concentration of unchanged DDAVP immediately before and, at intervals, up to 8 h after drug application, were analyzed by RIA.

Bioavailability was determined for each subject in a separate session by intravenous bolus injection of DDAVP (4 μg); blood samples were drawn before and up to 8 h after drug application and analyzed for DDAVP as described above.

For each of the volunteers DDAVP absorption in presence of aprotinin was found to increase about five-fold, i.e. from about 0.1% by weight to about 0.5% by weight, whereas the rate of absorption remained essentially constant. This suggests that the increased uptake is due to protection of DDAVP against proteolysis by gastric enzymes.

EXAMPLE 3

Tablets according to the invention containing selected amounts of DDAVP and aprotinin can be manufactured by slight modification (addition of aprotinin) of the method disclosed in EP-A-0 163 723. These tablets can be spray-coated with useful enteric coatings such as described by Agyilirah, G. A. and Banker, G. S. in Polymers for controlled drug delivery, Tarcha, P. J., Ed., CRC Press, Boca Raton 1991, p. 39–66.

EXAMPLE 4

Hard gelatin capsules containing a particulate enteric-coated DDAVP formulation according to the invention can be obtained in the following way. Solid core particles (100 g) prepared according to EP-A2-0 366 722 (example 3) are coated with 760 ml of an aqueous solution containing 20.0 mg DDAVP acetate and $7.10^5$ kallikrein-inhibiting units of bovine aprotinin (Antagosan®; Hoechst, Germany), and these coated particles are spray-coated in a Spheronizer® fluid-bed coater with a methanol - methylene chloride 1 : 1 coating solution containing (by weight) 10% of polyvinyl acetate phthalate (PVAP; TD-17, Colorcon Inc., West Point, Pa.), 0.7 of glyceryl triacetate and 1% of stearic acid, and dried. Hard gelatin capsules are filled with these enteric-coated particles (250 mg/capsule).

TABLE 1

| Peptide or peptide analog | Sequence |
|---|---|
| atosiban | Mpa—D—Tyr(Et)—Ile—Thr—Asn—Cys—Pro—Orn—GlyNH$_2$ (SEQ ID NO: 1) |
| carbetocin | Bua—Tyr(Me)—Ile—Gln—Asn—Cys—Pro—Leu—GlyNH$_2$ (SEQ ID NO: 2) |
| DDAVP (desmopressin) | Mpa—Tyr—Phe—Gln—Asn—Cys—Pro—D—Arg—Gly—GlyNH$_2$ (SEQ ID NO: 3) |
| oxytocin | Cys—Tyr—Ile—Asn—Cys—Pro—Leu—GlyNH$_2$ (SEQ ID NO: 3) |

I claim:

1. A pharmaceutical composition comprising a mixture of: a peptide selected from the group consisting of DDAVP (Desmopressin), atosiban, carbetocin, vasopressin, oxytocin, gonadorelin, and triptorelin; a protease inhibitor; and a pharmaceutically acceptable carrier which comprises a buffering agent, buffering at a pH of about 5.0, wherein said mixture is in the form of spheres each having a diameter smaller than about 2 mm, said spheres being coated with an enteric coat selected from polymers having dissociable carboxyl groups, making them readily soluble in gastric juice of about pH 5.0 and higher but not readily soluble at a substantially lower pH, said coated spheres being filled into capsules or tablets, and said capsules or tablets being readily disintegrable in the stomach.

2. The composition of claim 1, wherein the protease inhibitor is natural or structurally modified aprotinin.

3. The composition of claim 1, wherein the peptide is DDAVP.

4. Composition according to claim 1, wherein the pharmaceutically acceptable carrier further comprises at least one agent selected from the group consisting of carbohydrates, polyethylene and/or polypropylene glycol, inorganic fillers or lubricating agents, fatty acids and their esters and salts, preservatives and coating agents other than said enteric coating.

5. Composition according to claim 1, wherein said enteric coating is capable of releasing the contents of said composition in the upper part of the small intestine.

6. Composition according to claim 5, wherein said coating is designed for release in the duodenum and the jejunum.

7. Composition according to claim 5, wherein said coating is readily soluble in gastric juice and at above a pH of about 5.5 but not readily soluble at a substantially lower pH.

8. A method of manufacturing single doses of a composition comprising the following steps:

mixing a peptide selected from the group consisting of DDAVP (desmopressin), atosiban, carbetocin, vasopressin, oxytocin, gonadorelin, and triptorelin with a protease inhibitor and a pharmaceutically acceptable carrier which comprises a buffering agent, buffering at a pH of about 5.0, spheronizing the mixture for formation of spheres with a diameter smaller than about 2 mm, coating the spheres with an enteric coat selected from polymers having dissociable carboxyl groups, making them readily soluble in gastric juice of about pH 5.0 and higher but not readily soluble at a substantially lower pH, filling the coated spheres in capsules or incorporating them into tablets, said capsules or tablets being readily disintegrable in the stomach.

9. A method for administration of a single dose of a peptide selected from the group consisting of DDAVP (desmopressin), atosiban, carbetocin, vasopressin, oxytocin, gonadorelin, and triptorelin to a patient, comprising administering orally to the patient a tablet or capsule containing a pharmaceutically effective amount of said peptide in form of the composition according to claim 1, said tablet or capsule being readily disintegrable in the stomach and said peptide being released in the intestine.

10. A pharmaceutical composition prepared according to the method of claim 8.

* * * * *